United States Patent [19]

Nowak et al.

[11] Patent Number: 5,047,553
[45] Date of Patent: Sep. 10, 1991

[54] TETRAFLUORO-N-PHENYLPHTHALIMIDE

[75] Inventors: Deanne M. Nowak, Depew; Henry C. Lin, Grand Island, both of N.Y.

[73] Assignee: Occidental Chemical Corporation, Dallas, Tex.

[21] Appl. No.: 315,746

[22] Filed: Feb. 27, 1989

[51] Int. Cl.$^5$ .................. C07D 209/48; C07C 63/00; A61K 31/40
[52] U.S. Cl. ..................................... 548/476; 562/480
[58] Field of Search ................ 548/476, 473; 562/480; 514/417

[56] References Cited

U.S. PATENT DOCUMENTS 4,769,493  9/1988  Ito et al. ............................. 548/476

Primary Examiner—Alan L. Rotman
Assistant Examiner—Celia Chang
Attorney, Agent, or Firm—James F. Tao; Arthur S. Cookfair

[57] ABSTRACT

Chlorinated phthalic anhydrides are converted to fluorinated phthalic acids without dilactone formation by reacting an anhydride with a primary amine under anhydrous conditions to form the corresponding chlorinated-N-substituted phthalimide which in turn is reacted with a fluorinating agent under anhydrous conditions to form the corresponding fluorinated phthalimide which is hydrolyzed to form the corresponding fluorinated phthalic acid.

In a preferred embodiment tetrachlorophthalic anhydride is refluxed with aniline in the presence of glacial acetic acid for 5 to 10 hours to form tetrachloro-N-phenylphthalimide which is reacted with KF in sulfolane in the presence of tributylhexadecylophosphonium bromide under nitrogen at 140° C. to 160° C. for 10 to 15 hours to form tetrafluoro-N-phenylphthalimide which in turn is hydrolyzed by refluxing with 50% $H_2SO_4$ for 15 to 25 hours. The tetrafluoro-N-phenylphthalimide is a novel compound.

The fluorinated phthalic acid products are intermediates for the corresponding fluorinated phthalic anhydrides, fluorinated benzoic acids and fluorinated benzenes.

1 Claim, No Drawings

TETRAFLUORO-N-PHENYLPHTHALIMIDE

TECHNICAL FIELD

This invention is directed to a novel method of converting chlorinated phthalic anhydrides to corresponding fluorinated phthalic acids using imide intermediates.

In a preferred aspect, this invention is directed to a novel method of converting tetrachlorophthalic anhydride to tetrafluorophthalic acid and to a novel intermediate produced in said method, namely tetrafluoro-N-phenylphthalimide.

BACKGROUND OF THE INVENTION

The most direct route for converting chlorinated phthalic anhydrides to corresponding fluorinated compounds involves direct fluorination of the chlorinated anhydrides. Attempts at direct fluorination of tetrachlorophthalic anhydride (hereafter sometimes referred to as "TCPAN") have been reported in Odinokov, V. N. et al, *Zh. Obshch. Khim.*, 37(1), 176–181 (1967) as follows. When TCPAN was heated with potassium fluoride in boiling dimethylformamide, no tetrafluorophthalic anhydride was said to be obtained; the only product identified was octafluoroanthraquinone produced in 2% yield. When TCPAN was heated with anhydrous KF at 300° C. in the absence of solvent, octafluoroanthraquinone was said to be obtained in 40 to 45% yield and tetrafluorophthalic anhydride is not mentioned as a product. Furthermore, the inventors herein have tried the direct fluorination of TCPAN using the most recent advances in KF technology. The reaction was run in acetonitrile at 83° C. in the presence of a mixture of phase-transfer catalysts; the main products were dilactones and the yield of tetrafluorophthalic anhydride was only 1.4%.

It is an object herein to convert chlorinated phthalic anhydrides to fluorinated product without dilactone formation.

SUMMARY OF THE INVENTION

It has been discovered herein that chlorinated phthalic anhydrides can be converted to fluorinated phthalic acids without dilactone formation and in reasonable yields using imide intermediates. The fluorinated phthalic acid products are readily converted to the corresponding fluorinated anhydrides, fluorinated benzoic acids and fluorinated benzenes by conventional methods.

The process herein for converting a chlorinated phthalic anhydride to a corresponding fluorinated phthalic acid (by corresponding fluorinated phthalic acid is meant phthalic acid having fluorines in the same positions as the chlorines in the chlorinated phthalic anhydride starting material) comprises the steps of:

(a) reacting chlorinated phthalic anhydride having the formula:

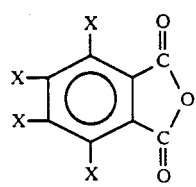

wherein each X is Cl or H and from 1 to 4 X's is Cl, with a primary amine having the formula $RNH_2$ wherein R is selected from the group consisting of $C_{1-12}$ alkyl, phenyl, $C_{1-12}$ monoalkyl-phenyl, naphthyl, and $C_{1-12}$ monoalkylnaphthyl, under anhydrous conditions to form chlorinated-N-substituted phthalimide having the formula:

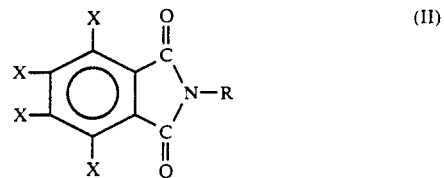

wherein X's correspond to those in (I) and R is the same as R in $RNH_2$, (b) reacting the phthalimide (II) with fluorinating agent under anhydrous conditions to replace each chlorine in said phthalimide (II) with fluorine to thereby form the corresponding fluorinated phthalimide, (c) hydrolyzing said fluorinated phthalimide to form the corresponding fluorinated phthalic acid, i.e., phthalic acid having the formula:

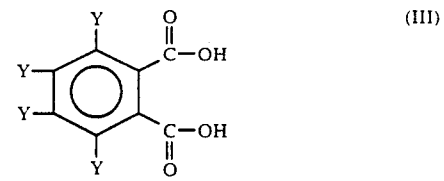

wherein Y is F or H with F in the same positions where X was Cl in (I) and H in the same positions where X was H in (I).

In a preferred aspect, the chlorinated phthalic anhydride (I) is tetrachlorophthalic anhydride, the primary amine, $RNH_2$, is aniline, the phthalimide (II) is tetrachloro-N-phenylphthalimide, the fluorinated phthalimide formed in step (b) is tetrafluoro-N-phenylphthalimide and the phthalic acid formed in step (c) is tetrafluorophthalic acid which is readily converted, for example, to tetrafluorophthalic anhydride or to 2,3,4,5-tetrafluorobenzoic acid or to 1,2,3,4-tetrafluorobenzene. The intermediate fluorinated imide, i.e., tetrafluoro-N-phenylphthalimide, is a novel compound.

DETAILED DESCRIPTION

The chlorinated phthalic anhydride (I) includes, for example, 3-monochlorophthalic anhydride, 4-monochlorophthalic anhydride, 3,4-dichlorophthalic anhydride, 3,5-dichlorophthalic anhydride, 3,5-dichlorophthalic anhydride, 3,4,5-trichlorophthalic anhydride, 3,4,6-trichlorophthalic anhydride, 3,5,6-trichlorophthalic anhydride, 4,5,6-trichlorophthalic anhydride and tetrachlorophthalic anhydride. A preferred chlorinated phthalic anhydride (I) is tetrachlorophthalic anhydride.

The primary amine for step (a) can be, for example, methylamine, isopropylamine, dodecylamine, aniline, 4-tert-butylamine, 3-decylaniline, 1-naphthylamine, 2-naphthylamine, 1-amino-4-methylnaphthalene, 1-amino-5-methylnaphthalene, 2-amino-3-ethylnaphthalene and 2-amino-5-hexylnaphthalene. A preferred primary amine for step (a) is aniline.

Step (a) is preferably carried out with an equimolar amount or slight excess of primary amine in the absence of solvent in the presence of an acidic catalyst, such as glacial acetic acid. Other acidic catalysts include, for example, trichloroacetic acid, trifluoroacetic acid, propionic acid, p-toluenesulfonic acid and acidic ion-exchange resin. This acid catalyzed reaction is typically carried out at a temperature ranging from 50° C. to the reflux temperature over a period of about 2 to 20 hours. For reaction of tetrachlorophthalic anhydride with aniline in the presence of glacial acetic acid, the reaction is preferably carried out at reflux temperature (114° C.) over a period of 5 to 10 hours.

Step (a) can also be carried out by reacting with or without the use of solvent (such as toluene or benzene) to azeotropically remove water which is generated.

We turn now to step (b). The fluorinating agent can be, for example, KF, CsF, tetra-n-butyl-ammonium fluoride, $KF/CF_2$, or AgF. For economy KF is preferred. The fluorination can be carried out in the solid phase, or with a non-polar solvent (e.g., dichlorobenzene, xylene or trichlorobenzene) or preferably with a dipolar aprotic solvent (e.g., sulfolane, dimethylsulfoxide, N-methylpyrrolidone, acetonitrile, dimethyl sulfone, dimethyl formamide or dimethyl acetamide). Very preferably the fluorination is carried out in sulfolane. The reaction typically is run with an excess of fluorinating agent at 50°-200° C. over a time period ranging from about 6 to 72 hours in the presence of the a phase transfer catalyst, for example, tetraalkylammonium or phosphonium halides, typically tri $C_{1-4}$ alkyl mono $C_{10-18}$ alkyl ammonium or phosphonium halides, and polyether phase transfer catalysts such as crown ethers. For fluorinating tetrachloro-N-phenylphthalimide with KF in sulfolane in the presence of the phase transfer catalyst, tributylhexadecylphosphonium bromide, the reaction is preferably carried out at 130° C. to 190° C., very preferably over a period of 10-15 hours at 145° C. to 160° C. To assure anhydrous conditions, step (b) is preferably carried out in an inert atmosphere, preferably under nitrogen.

We turn now to step (c), that is, the hydrolysis step. This step can be carried out by heating in the presence of an aqueous base or an aqueous acid, e.g., at a temperature ranging from 80° C. to reflux temperature as determined by acid or base strength. Hydrolysis of tetrafluoro-N-phenylphthalimide to provide tetrafluorophthalic acid is preferably carried by refluxing for 15 to 25 hours with 50% aqueous $H_2SO_4$; purification is readily carried out by dissolution in aqueous base followed by reprecipitation with aqueous acid and/or by recrystallization.

The product fluorinated phthalic acid can be converted to the corresponding anhydride by azeotropic water removal using benzene or by refluxing with trifluoroacetic anhydride.

The product fluorinated phthalic acid can be converted to the corresponding fluorinated benzene by completely decarboxylating by heating, e.g., at a temperature ranging from 100° C. to 250° C. with soda lime. These fluorinated benzenes have use as insecticide and larvicide intermediates.

The fluorinated phthalic acid product herein can be converted to the corresponding fluorinated benzoic acid, for example, by refluxing in dimethylformamide. For example, tetrafluorophthalic acid is converted to 2,3,4,5-tetrafluorobenzoic acid (TFBA) by refluxing with dimethylformamide for 20 to 30 hours to form crude TFBA followed by purification of the crude TFBA by refluxing with 50% $H_2SO_4$ acid for 15 to 20 hours. Tetrafluorophthalic acid can also be converted to TFBA by heating in dimethylsulfoxide (Yacobson, G. G. et al, *Zh. Obshch. Khim.*, 36(1), 139-142 (1966) or by heating in an aqueous medium in which the pH is controlled at 0.7 to 2.2 (European Patent Application Publication 194671). TFBA is an intermediate for drugs and pesticides. For example, it is an intermediate for preparation of trifluoroquinolinone which is a bactericide.

The invention is illustrated in the specific examples which follow.

EXAMPLE I

Tetrachlorophthalic anhydride (300 g, 1.05 moles) was combined with aniline (100 g, 1.08 moles) and glacial acetic acid (3750 ml) in a 3-neck round bottom flask fitted with a cold-water condenser, overhead stirrer and a thermometer. The mixture was allowed to reflux (114° C.) with stirring for 6.5 hours. Crystallization occurred upon cooling. The crystals were filtered, washed with cold water and dried at 120° C., 0.5 mm Hg for 18 hours. 366 g tetrachloro-N-phenylphthalimide (96% yield) were recovered, mp 274°-275° C. The product was identified by gc/ms.

Tetrachloro-N-phenylphthalimide (100 g, 0.28 moles) was combined in a nitrogen atmosphere with 193 g KF (3.3 moles; dried 48 hours at 300° C., 1 mm Hg), 4 g tributylhexadecylphosphonium bromide (0.049 moles, dried 16 hours at 150° C., 0.5 mm Hg) and 413 g sulfolane (freshly distilled from $CaH_2$) in a 3-neck round-bottom flask fitted with a cold-water condenser, overhead stirrer and thermometer. The reaction was run under a positive pressure of $N_2$ at 145°-159° C. for 12.3 hours. The mixture was filtered hot and the filter cake washed with acetone. Acetone was flash evaporated from the distillate. The product was separated from the sulfolane by addition of the filtrate to 1900 ml distilled water. The solid was filtered and dried at 80° C., 1 mm Hg giving 88.1 g crude tetrafluoro-N-phenylphthalimide. The yield was 74%, determined by $^{19}F$ NMR using 3-fluorotoluene as the internal standard. Purification by bulb-to-bulb distillation (150°-190° C., 1 mm Hg) followed by recystallization from tetrahydrofuran/water resulted in a white crystalline solid (mp 210°-211° C.: Calculated for $C_{14}H_5NO_2F_4$; C, 56.96; H, 1.71; N, 4.74; F, 25.74%; Found: C, 56.95; H, 1.78; N, 4.68; F, 24.60%. The product was identified by $^{19}F$ NMR and gc/ms.

Combined with 38.4 g recrystallized tetrafluoro-N-phenylphthalimide (0.13 moles) were 208 g 50% sulfuric acid and this combination was allowed to reflux (122° C.) for 19 hours. The solution was extracted with ether. The ether layer was dried over anhydrous $MgSO_4$ and the ether was removed by flash evaporation. 31.03 g crude tetrafluorophthalic acid was recovered. The product was identified by gc/ms. This product can be purified by dissolving in aqueous base, followed by reprecipitation with aqueous acid and/or by recrystallization.

EXAMPLE II

When in Example I, an equimolar amount of dodecylamine, or 4-tert-butylamine or 1-naphthylamine or 2-naphthylamine or 1-amino-4-methylnaphthalene is substituted for the aniline, production of similar yields of tetrafluorophthalic acid is obtained.

EXAMPLE III

When in Example I, an equimolar amount of CsF is used in place of the KF or equimolar amount of trimethylhexadecyl-ammonium chloride or crown ether is substituted for the tributyl-hexadecylphosphonium bromide or an equal volume of dimethylsulfoxide or N-methylpyrrolidone or acetonitrile is substituted for the sulfolane, production of similar yields of tetrafluorophthalic acid is obtained.

EXAMPLE IV

When in Example I, an equimolar amount of 3,5,6-trichlorophthalic acid is substituted for the tetrachlorophthalic anhydride, the product is 3,5,6-trifluorophthalic acid. The 3,5,6-trifluorophthalic acid is converted to 1,2,4-trifluorobenzene by refluxing for 12 hours with soda-lime.

EXAMPLE V

The crude tetrafluorophthalic acid obtained in Example I can be converted to 2,3,4,5-tetrafluorobenzoic acid without purification as illustrated by the following.

31.03 g crude tetrafluorophthalic acid (0.13 moles) were combined with 78 ml dimethylformamide and stirred at 145° C. for 25 hours. The dimethylformamide was removed by distillation (90°–106° C., 93–50 mm Hg) and the crude tetrafluorobenzoic acid was isolated by bulb-to-bulb distillation (100°–105° C., 0.3 mm Hg). 17 g crude tetrafluorobenzoic acid was purified by refluxing in 168 g 50% sulfuric acid for 18 hours. The mixture was then extracted with diethyl ether. 6.24 g white solid was obtained. Recrystallization from hexane resulted in 4.68 g 2,3,4,5-tetrafluorobenzoic acid (mp 90°–91° C.). The purity of the product was established to be 99% by $^{19}F$ NMR.

EXAMPLE VI

Tetrafluorophthalic acid is converted to tetrafluorophthalic anhydride by refluxing for 12 hours with a slight excess of trifluoroacetic acid.

Variations will be evident to those skilled in the art. Therefore, the scope of the invention is intended to be defined by the claims.

What is claimed is:

1. Tetrafluoro-N-phenylphthalimide.

* * * * *